(12) United States Patent
McClure et al.

(10) Patent No.: US 6,318,387 B1
(45) Date of Patent: *Nov. 20, 2001

(54) PARTS WASHING SYSTEM

(75) Inventors: James C. McClure, Norcross; J. Leland Strange, Duluth; Thomas W. McNally, Norcross; Francis A. Marks, Atlanta, all of GA (US)

(73) Assignees: Advanced Bioremediation Systems, Inc., Duluth; Chemfree Corporation, Norcross, both of GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/867,586

(22) Filed: Jun. 2, 1997

Related U.S. Application Data

(63) Continuation of application No. 08/370,898, filed on Jan. 10, 1995, now abandoned, which is a continuation of application No. 08/315,902, filed on Sep. 30, 1994, now abandoned.

(51) Int. Cl.[7] ......................................................... B08B 3/02
(52) U.S. Cl. ......................... 134/111; 134/108; 134/109; 435/264; 210/610
(58) Field of Search ..................................... 134/111, 109, 134/201, 108; 210/610; 435/264

(56) References Cited

U.S. PATENT DOCUMENTS

| 3,378,019 |   | 4/1968  | Riolo et al. ........................... 134/111 |
| 3,522,814 | * | 8/1970  | Olson .................................... 134/111 |
| 3,960,728 |   | 6/1976  | Otzen .................................... 210/167 |
| 3,970,560 |   | 7/1976  | Metzger ................................ 210/167 |
| 4,925,564 | * | 5/1990  | Francis ................................. 210/610 |
| 5,039,415 |   | 8/1991  | Smith .................................... 210/611 |
| 5,225,083 | * | 7/1993  | Pappas et al. ........................ 210/610 |
| 5,303,725 | * | 4/1994  | Hilgren ................................. 134/111 |
| 5,314,620 | * | 5/1994  | Staniec ................................. 210/610 |
| 5,376,183 | * | 12/1994 | Gatt et al. ............................. 210/610 |
| 5,401,413 | * | 3/1995  | Gatt et al. ............................. 210/610 |
| 5,492,139 | * | 2/1996  | Lashmett et al. ..................... 134/111 |

FOREIGN PATENT DOCUMENTS

| 4209052 A1 | 2/1993  | (DE) . |
| 2014286    | 5/1990  | (RU) ................................ C02F/3/34 |
| 1496841    | 7/1989  | (SU) ................................ B08B/3/02 |
| 80983      | 11/1956 | (SU) ................................ B08B/3/10 |
| 452392     | 4/1975  | (SU) ................................ B08B/3/10 |

\* cited by examiner

*Primary Examiner*—Frankie L. Stinson
(74) *Attorney, Agent, or Firm*—Barnes & Thornburg; Alice O. Martin

(57) ABSTRACT

Provided is a system for parts washing that includes a fluid that performs a cleaning function and maintains the viability of microorganisms in the fluid that biodegrade the organic matter removed from the parts. "Parts" include objects such as automotive parts befouled with organic matter and particulate matter. The cleaning fluid includes a surfactant that functions to separate organic waste from the parts being washed. The cleaning fluid is both in a cleaning area and in a housing for microorganisms. A heater, thermostat, and a level control assembly function to maintain the cleaning fluid within a certain temperature range so as to maintain a proper environment for the microorganisms. The fluid recirculates from the microorganism housing to the parts cleaning area.

6 Claims, 4 Drawing Sheets

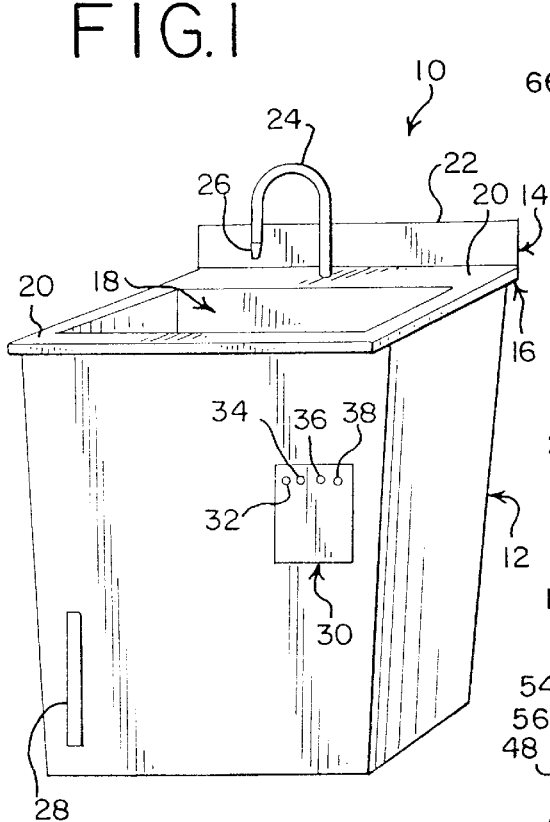
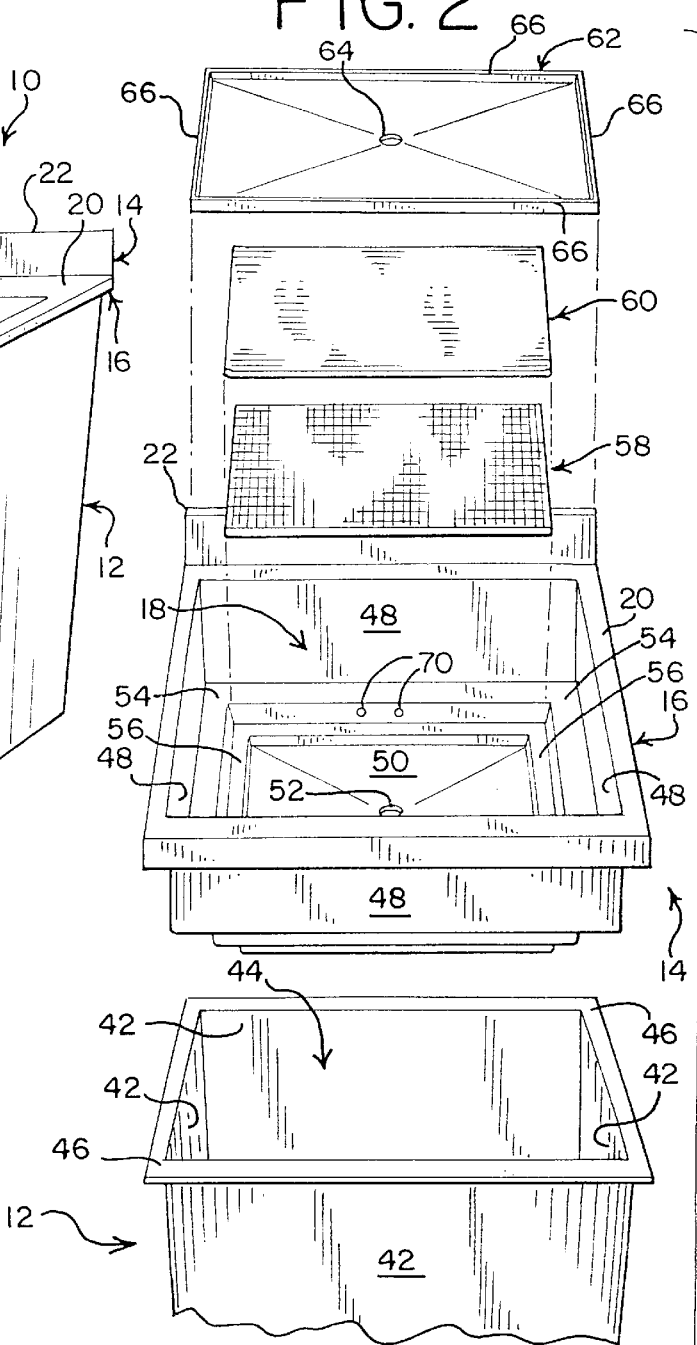

PARTS WASHING SYSTEM

The present application is a continuation of copending U.S. Ser. No. 08/370,898 filed Jan. 10, 1995 abandoned which is a continuation of copending U.S. Ser. No. 08/315,902, filed Sep. 30, 1994 now abandoned.

BACKGROUND OF THE INVENTION

A parts washer including a mechanical, fluid and a biological component, reduces environmental problems of waste disposal. "Parts" include objects fouled with organic and particulate matter such as automotive parts.

Parts washers are employed in the cleaning of parts that are contaminated with organic waste products such as hydrocarbons, oils, greases, road dust and grit. The type of parts washed in a parts washer include automotive parts such as nuts, bolts, valves, pistons, carburetors, transmission parts, and the like. Most conventional parts washers include a basin mounted on the top of a tank. The tank is partially filled with a mineral spirits solvent that is pumped from the tank through a conduit that discharges into the basin where the parts are washed. The mineral spirits solvent drains from the basin back to the tank for reuse. A filter is sometimes interposed in the solvent flowpath to collect organic waste products and particulates washed from the parts.

Although mineral spirits are an effective cleaning solvent, there are many drawbacks to the employment of parts washers that utilize mineral spirits. For example, mineral spirits solvents are presently classified by government regulatory agencies as hazardous materials because of their low flash point and potential health concerns. For example, contact dermatitis is common for operators of parts washers who generally do not wear gloves. Because of this classification, mineral spirits must be used, handled, and disposed of in compliance with extensive government regulations. Further, mineral spirits that are not properly contained can have a negative impact on the immediate work environment, and it is not uncommon for workers to have dermatitis and respiratory problems exacerbated by the unprotected use of mineral spirits. Additionally, many users of mineral spirits find it necessary to dispose of used mineral spirits by having a licensed waste disposal company pick up the used mineral spirits so that the used mineral spirits can be disposed of in compliance with the various governmental guidelines and regulations; such disposal can be expensive.

Filters are generally incorporated into conventional parts washers to separate the organic waste products and particulates from the solvent. A problem is that the filters eventually become saturated with organic waste products and particulates and therefore need to be replaced. The filters are often difficult to access and replace. Furthermore, the filters, after they have absorbed the organic waste products, are often considered hazardous material and are therefore difficult to dispose of according to legal restrictions.

There is, therefore, a need in the industry for a system which provides for parts washing and reduces environmental problems associated with mineral spirits as a cleaning (washing) component.

SUMMARY OF THE INVENTION

A system for parts washing employs a combination of a cleaning fluid and a biological agent as a method to replace the mineral spirits of other parts washers. "Parts" as used herein include objects befouled with organic and/or particulate matter. Parts cleaned according to the invention include automotive parts, equipment parts and machinery parts. Objects are inanimate, non-biological objects such as metal or plastic. The cleaning fluid serves two purpose: 1) cleans parts; and 2) maintains the viability of the biological agent. An apparatus is developed that is suitable for implementation of the method.

The cleaning fluid includes a surfactant that functions to remove organic waste from the parts being washed. The biological component includes microorganisms that digest the organic waste. The cleaning fluid is not toxic to the microorganisms, therefore the microorganisms survive and reproduce within the cleaning fluid environment. The present invention comprises a parts washing system characterized by a cooperative interaction among a mechanical component, a fluid component, and a biological component. The parts washer apparatus (herein also referred to as the "parts washer") of the parts washing system includes, a holding tank, cleaning fluid retained within the tank, microorganisms living with the cleaning fluid, a wash basin, a fluid delivery system, an in-line filter to which microorganisms are affixed, and an electrical control system for maintaining an environment conducive to maintaining and promulgating the life of the microorganisms.

In an illustrative embodiment, the wash basin of the parts washer is a multi-tiered basin including a sink member defining a bottom panel and a false bottom disposed above the bottom panel. The multi-tiered basin further includes a support grid and filter interposed between the false bottom and the sink member. The false bottom, support grid, and filter are readily removable from the sink member. The holding tank is partially filled with the cleaning fluid, and a pump and conduit assembly direct a flow of the cleaning fluid to the basin. The cleaning fluid discharged into the basin flows through a drain hole in the false bottom, through the filter and support grid, and then through a drain hole defined through the bottom panel of the sink member, finally the cleaning fluid is then returned to the tank for reuse. The pump and conduit assembly functions to aerate the cleaning fluid; and a heater, thermostat, and level control assembly function to maintain the cleaning fluid within a certain temperature range so as to maintain a proper environment for the sustainment of the microorganisms. The microorganisms are preferably introduced into the cleaning fluid in a dormant state. The microorganisms in the dormant state are preferably adhered to the filter prior to use, for example by an adhesive, and released from the filter when the cleaning fluid flows through the filter by dissolution of the adhesive and the force of the flow. For example, a microorganism "sandwich" is made by spraying an adhesive layer on the filter, dusting powdered microorganisms over the adhesive then spraying the microorganism layer with an adhesive layer.

The present invention optionally includes retrofit components to parts washers currently using mineral spirits. A conversion kit consisting of the cleaning fluid, a thermostatic heating element, a filter pack with dormant microorganisms, and special adapter fittings is used to convert a parts washer using a method of cleaning other than that of the present invention, to the biodegrading system of this invention. Adaptations of the kit can be specifically tailored for; tumblers, vibrator cleaners, and other agitation systems including those using fluid jet and sprays that also presently use mineral spirits.

An ultrasonic tank and brushes may work in conjunction with the cleaning fluid to expedite the breaking up of encrusted organic waste and particulates. For example, an electrically driven ultrasonic transducer located in the base of a brush may act alone or in combination with one or more larger (or macro) motions which, include vibration of brush bristles axially or rotationally, and continuous rotation of the brush bristles about one or more axis. Power is derived from either electrical or fluid turbine components.

In summary the present invention provides a new system for washing parts. A biological component is sustained within the parts washer by means of the fluid component, which also has a cleaning function. The parts washing system is "environmentally friendly," for example, it decreases the production of hazardous waste materials. Organic waste is broken down into its non-contaminating components by the combined action of the fluid component and the biological component. The parts washer system does not require frequent fluid replacement due to recirculation. The only fluid loss is that due to evaporation. Structurally, the apparatus of the present invention is a parts washer with a multi-tiered sink structure, and a readily accessible and replaceable filter. Parts are washed and resultant organic waste is continuously recirculated in a closed, self contained environment. Consequently, the need for disposal of organic waste washed from parts is greatly reduced; in fact, generally eliminated.

An advantage of the parts washing system is that it does not employ a volatile and flammable cleaning fluid, in contrast to most conventional parts washers. Consequently, an automatically closing lid is not required on the parts washer of the present invention to isolate the cleaning fluid in case of a shop fire.

Users of the invention attest that it is "kind to hands". In fact, instead of needing to wash their hands many times as necessitated by mineral spirits contact, the parts washer of the present invention, actually cleans the users' hands.

Other features and advantages of the present invention will become apparent upon reading and understanding the specifications, taken in conjunction with the accompanying drawings.

BRIEF DESCRIPTION OF THE DRAWINGS

FIG. 1 is an exterior perspective view of a parts washer in accordance with the present invention.

FIG. 2 is a cut-away, perspective, exploded view of isolated components of the parts washer of FIG. 1.

DETAILED DESCRIPTION OF THE PREFERRED EMBODIMENT

Figure 3:
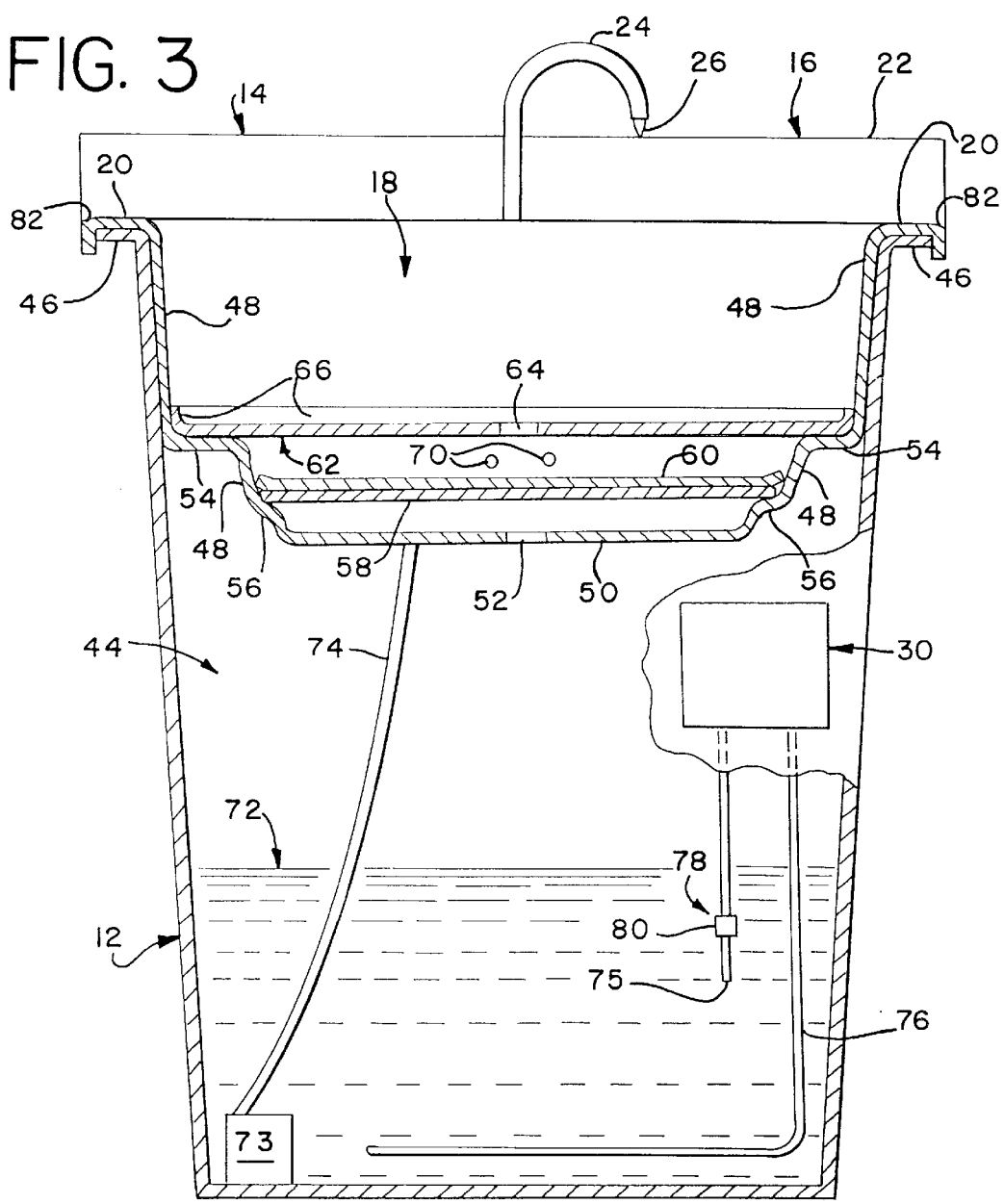
FIG. 3 is a front, vertical cross-sectional, cut-away view of the parts washer of FIG. 1, wherein certain portions of the parts washer are not cross-sectioned or cut-away.

Referring now in greater detail to the drawings in which like numerals represent like components throughout several views, FIG. 1 is an exterior, perspective view of a parts washer apparatus (the "parts washer") 10, in accordance with an embodiment of the present invention. The parts washer 10 includes a tank 12 and a basin 14. The basin 14 includes a sink member 16 that defines a basin cavity 18. The sink member includes a sink ledge 20 around the periphery of the inlet to the basin cavity 18. A back-splash 22 extends upward from a rear portion of the sink ledge 20, and a flexible faucet 24 penetrates the rear portion of the sink ledge 20 and terminates in the form of a nozzle 26. An optional work light (not shown) extends upward from the basin and illuminates the basin cavity 18. The tank 12 includes an optional level indicator 28 and a control panel 30. The level indicator 28 is depicted as comprising a temperature sensitive, liquid crystal display. The control panel 30 includes an off/on switch 32, a power indicator light 34, a low fluid warning light 36, and a timer switch 38. This timer switch 38 serves to keep the circulation of the fluid limited to the time when parts are actually being washed. Studies of parts washing operators cleaning a variety of parts containing varying amount of soil indicated that a four minute time interval allows the flow to run sufficiently to clean about eight-five percent of all parts. Longer flow intervals, if required, are accomplished by reactivating the run switch.

FIG. 2 is a cut-away, perspective, exploded view of certain components of the parts washer 10, in accordance with the present invention. A lower portion of the tank 12, and components associated therewith, and the faucet 24 are cut-away in FIG. 2. The tank 12 includes tank walls 42 that define a tank cavity 44 therebetween. The tank 12 further includes a tank lip 46 that extends around the periphery of the inlet to the tank cavity 44. The sink member 16 includes sink walls 48 extending downward from the sink ledge 20 to a bottom panel 50 that defines a drain hole 52 therethrough. The sink walls 48 and the bottom panel 50 define the basin cavity 18. The sink walls 48 further define an upper ledge 54 and a lower ledge 56. Each of the ledges 54, 56 encircle the basin cavity 18 and include four segments that together define a rectangular shape. Each edge of a planar, rectangular support grid 58 rests upon a segment of the lower ledge 56 such that the support grid 58 partitions the basin cavity. A rectangular filter pad 60 rests upon and covers the support grid 58. Each edge of a generally planar, rectangular false bottom member 62 rests upon a segment of the upper ledge 54 such that the false bottom member 62 also partitions the basin cavity 18 and is disposed above the support grid 58. The false bottom member is preferably unitary, defines a drain hole 64 therethrough and includes an upwardly protruding lip around the periphery thereof. A strainer (not shown) is defined within the drain hole 64. A pair of supplemental drain holes 70 are defined through the rear sink walls 48 just above the filter pad 60. This embodiment comprising the false bottom member 62, the filter pad 60, the filter support grid 58, and drain holes 64, 52, 70, serves to limit evaporative losses caused by the elevated temperature of the cleaning fluid.

FIG. 3 is a front, vertical cross-sectional, cut-away view of the parts washer 10, wherein certain portions of the parts washer are, for explanatory purposes, not cross-sectioned or cut-away. FIG. 3 represents each of the mechanical components (i.e. the hardware, or "parts washer" 10 as herein described), the fluid component (represented by a cleaning fluid 72), and the biological component (not seen) living within the cleaning fluid 72. As depicted in FIG. 3, the periphery of the false bottom member 62 preferably snugly contacts the sink walls 48. The tank cavity 44 is preferably partially filled with a cleaning fluid 72. A submersible pump 73 is disposed within the tank cavity 44. When pump 73 is operating, it draws the cleaning fluid 72 from the bottom region of the tank cavity 44 and discharges the cleaning fluid 72 into a conduit 74. The conduit 74 is connected to and discharges into a base (not shown) of the faucet 24, whereby the fluid discharges from the nozzle 26. The parts washer 10 is preferably further equipped with optional cleaning accessories (not shown) such as a fountain brush (not shown) that is in fluid communication with the conduit 74. A heater 76, that is controlled by a thermostat 75, selectively heats the cleaning fluid 72, and the heater 76 is acceptably in the form of an electric heating element that extends from the control panel 30 into the depths of the tank cavity 44. A level probe monitors the depth of the cleaning fluid 72, and the level probe is acceptably in the form of a float actuated electric switch 78 that includes a magnet equipped float 80. A lip 82 extends around the periphery of the sink ledge 20 forward of the back-splash 22. The lip 82 and back-splash 22 seek to keep cleaning fluid from dripping over the edges of the sink ledge 20. In accordance with a preferred construction of the present invention, much of the parts washer 10 is acceptably constructed from high density polyethylene. In addition, the sink walls 48, bottom panel 50, upper ledge 54, lower ledge 56, sink ledge 20, and back-splash 22, are preferably formed as a single, molded, unitary piece.

Optionally, the apparatus may be equipped with a tank 12 containing a pre-treatment compartment. This compartment receives fluid pumped from the bottom region of the tank cavity 44. By holding this fluid in the proper environment for as long as needed to virtually eliminate oil and grease, this compartment allows discharge of waste into publicly operated treatment facilities.

The biological component is preferably in the form of microorganisms that biodegrade organic compounds such as, hydrocarbons, oils, greases, petroleum by-products, creolates, and other carbon based compositions. Microorganisms which degrade other carbon based compositions such as the long-chain polymers compounds found in structural plastics such as the polyolefins, styrenes, neoprenes, and the like are not suitable if the physical structure of the parts washer or of parts being washed is degradable by the microorganisms. The microorganisms generally convert hydrocarbon compounds and chlorinated solvents into elements of water, carbon dioxide and other digestion products. Additionally, the microorganisms are preferably nonpathogenic. Suitable microorganisms include those from the genera Bacillus, Micrococcus, Acinetobacter, Rhodococcus, Nocardia, Flavobacterium, Saccharomyces, Candida and White Rot Fungus. Suitable species are well known and reported in the art. The microorganisms are optionally employed in combination with nitrifying or denitrifying bacteria, phosphate solubilizing strains of microorganisms, bio-emulsifier producing strains of microorganisms, and strains of microorganisms which produce growth factors such as, B-vitamins.

The microorganisms are preferably subjected to a preservation technique in an effort to ensure their viability in the field and their resistance to environmental shock. For example, nutrient and buffer components such as, agar, and water soluble adhesives such as gum are preferably mixed with the microorganisms to promote stability of the microorganisms prior to mixing the microorganisms with a carrier. The carrier is composed of inert and nutrient organic materials that preserve and protect the microorganisms during storage and transportation. Suitable microorganisms are available from ABS Inc. of Duluth, Ga. as, for example, Part Number PWM-25 or from Louisiana Remediation as LRC-1.

The filter pad 60 functions as a vehicle for bringing the microorganisms into contact with the cleaning fluid 72. The filter pad 60 is constructed from cotton, cellulose, polyolefin fibers, polyester fibers, fiberglass, or the like. Additionally, the filter pad 60 is constructed from combinations of such components. Further, the filter pad 60 is generally a 10 micron filter or larger. Microorganisms are attached to the filter pad 60 with an encapsulating agent 84 (FIG. 4) that is water soluble and releases the microorganisms when the cleaning fluid 72 is introduced to the filter pad 60, as discussed below. An adhesive suitable for this purpose is 3M Super 77 adhesive.

Figure 4:
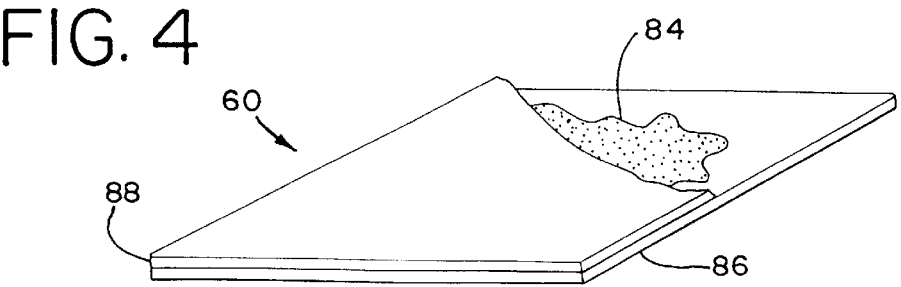
FIG. 4 is a perspective, cut-away view of a filter pad portion of the parts washer in accordance with the present invention.

Referring to FIG. 4, which is a perspective, cut-away view of the filter pad in accordance with the present invention, the filter pad 60 includes a layer 86 of inert material, that is disposed below a layer 88 of micron-rated filter media. A suitable inert material is fiberglass. The micron rated material is preferably a material that does not have an affinity for hydrocarbons such as, for example polyester. The microorganisms, the components mixed therewith as discussed above, and the adhering agent 84 are preferably sandwiched between the layers 86, 88 of the filter pad 60. A portion of the layer 88 is cut-away for explanatory purposes in FIG. 4 such that the adhering agent 84 is seen. After the microorganisms are attached to the filter pad 60, the filter pad 60 is then acceptably stored until its usage within the parts washer 10 is desired. In accordance with an embodiment of the present invention, the microorganisms are added directly to the cleaning fluid 72 without being initially attached to the filter pad 60. Thus, the filter pad 60 functions, as both a mechanical filter (i.e., straining particulate matter from the fluid 72) and as an initial transport medium for the microorganisms, or the filter pad 60 functions solely as a mechanical filter.

The cleaning fluid 72 is compatible with (i.e., non-toxic to) the microorganisms such that the microorganisms are capable of living within the cleaning fluid 72. Additionally, the cleaning fluid 72 tends to separate organic waste from parts washed in the basin 14, as will be discussed in greater detail below. A suitable cleaning fluid 72, for example, is a mixture of pH neutral emulsifiers and surfactants containing no volatile organic compounds, phosphates, formaldehyde, biocides, or other toxic materials. The emulsifier and surfactants are blended in liquid form to produce a biodegradable, non-toxic, non-caustic, non-flammable oil dispersant cleaner and degreaser. In addition the cleaning fluid 72 preferably contains no known carcinogens, no Occupational Safety and Health Act (OSHA) or Department of Transportation (DOT) regulated chemicals, no ingredients requiring Superfund Amendments and Reauthorization Act Title III reporting (SARA Title III), no Solid Waste Disposal Act as amended by the Resources and Conservation Recovery Act of 1976 as amended, 42 USC Section 6901 et seq. (RCRA), and no items on the Comprehensive Environmental Response, Compensation and Liabilities Act (CERCLA) hazardous substance list. In an illustrative embodiment, the exemplary cleaning fluid 72 is a free flowing liquid with a specific gravity of 1.083, a slight pleasant odor, no flash point, a boiling point of 210 degrees Fahrenheit, a pH of approximately seven, and is infinitely soluble in water. A suitable cleaning fluid is available from Warren Chemical Corporation of Robert, La. as Sea Wash 7 (Solvent #5 in Table 1) or Safeworld Products SW-2.

Referring further to FIG. 3, in operation, the pump 73, conduit 74, and faucet 24 circulate cleaning fluid 72 from the depths of the tank cavity 44 to the basin 18 where parts cleaning takes place. The false bottom member 62 is preferably sufficiently sturdy and well supported such that a variety of parts are capable of being placed thereon for cleaning. In an embodiment, cleaning fluid 72 flows out of the nozzle 26 and the part being washed is oriented within the stream of cleaning fluid 72 exiting the nozzle 26. The cleaning fluid 72 separates organic waste from the part being washed, and then the cleaning fluid 72, along with the organic waste and any small particulate washed from the part, flows by gravity through the drain hole 64 and the strainer (not shown) associated therewith. The strainer will, of course, keep certain objects from passing through the drain hole 64. The cleaning fluid 72, organic waste, and remaining matter then encounter the filter pad 60. Subsequently, the fluid 72 and the organic contaminants pass through the support grid 58, and drain hole 52 to deposit into the tank cavity 44. Should flow through the filter pad 60 become obstructed, flow will divert through the pair of supplemental drain holes 70 defined through the rear sink wall 48 just above the filter pad 60. The filter pad 60 functions is to trap the particulate matter and allow the organic contaminants and cleaning fluid 72 to pass therethrough. Because the filter pad 60 does not collect the organic contaminants, it is capable of being disposed of as solid waste. If the filter pad 60 is new or relatively new such that all of the microorganisms have not been previously released therefrom, the cleaning fluid 72 releases the dormant microorganisms attached to the filter pad 60, and the released microorganisms flow with the cleaning fluid 72 and organic contaminants through the drain hole 52 into the tank cavity 44. Within the tank cavity 44, a large percentage of the microorganisms and organic contaminants will tend to accumulate proximate to the surface of the cleaning fluid 72 such that a large portion of the biodegradation takes place proximate to the surface of the cleaning fluid 72. This forms a vapor barrier that tends to minimize the evaporation of the cleaning fluid 72. If living microorganisms are not present in the parts washer 10, increasing amounts of organic waste will accumulate toward the surface of the cleaning fluid 72 in the tank cavity 44, and this condition is indicative of the need to replenish the microorganisms. However, if the parts washer 10 is used for normal parts cleaning, it should not be necessary to add new microorganisms to the cleaning fluid 72 of the parts washer 10. Nonetheless, by virtue of the fact that the filter pad 60 is the vehicle for adding microorganisms to the cleaning fluid 72, as discussed above, microorganisms are added to the cleaning fluid 72 each time a new filter pad 60 is added to the parts washer 10, as discussed in greater detail below. By virtue of the microorganisms digesting the organic waste within the tank 12, the cleaning fluid 72 is "recirculated" within the parts washer 10, whereby the cleaning fluid 72 has the potential to last for extended periods of time. It is likely, however, that some cleaning fluid 72 replenishment will be required, however, to make up for evaporative and "drag-out" losses incurred as parts are removed from the basin cavity 18 in wet condition. Furthermore, by virtue of the cooperative effect of the filter pad 60 (removing particulate matter) and the microorganisms (digesting organic waste), the tank is, potentially, seldom in need of "dredging" to remove waste.

Referring back to FIGS. 1 and 3, when the off/on switch 32 is in the on position, electricity is supplied to circuitry (not shown) which is housed within the control panel 30 by way of a conventional power cord (not shown), and the indicator light 34 is illuminated. After the off/on switch 32 is in the "on" position, the circuitry, in combination with the thermostat 75, activates and deactivates the heater 76. While the thermostat 75 senses that the temperature of the cleaning fluid 72 within the tank cavity 44 is below a desired temperature, the heater 76 is on, and while the thermostat 75 senses that the temperature of the cleaning fluid 72 is at or above the desired temperature, the heater 76 is off. The cleaning fluid 72 is preferably maintained in a temperature range which supports the lives of the particular microorganisms employed within the parts washer 10. The temperature is preferably maintained in the mesophilic range of approximately 75° to 115° Fahrenheit. The float actuated electric switch 78 also controls the operation of the heater 76. When the magnet equipped float 80 drops downward due to a low level of the cleaning fluid 72, the switch 78 is actuated which, in combination with the circuitry, disables the heater 76 and causes the low level warning light 36 to illuminate. Operation of the pump 73 is controlled by the timer switch 38. A user can manually actuate the timer switch 38 which, in combination with the circuitry, causes the pump 73 to operate and automatically cut off after a certain period of time. In accordance with an alternative embodiment of the present invention, an additional switch (not shown) is provided that overrides the timer switch 38 such that the pump 73 will remain running as long as the additional switch is "on".

Referring back to FIGS. 2 and 3, the parts washer 10 is designed to provide easy access to the filter pad 60. Access is obtained by simply lifting the false bottom member 62 out of the basin cavity 18. There is generally no restrictive engagement between any components that are depicted as exploded away from each other in FIG. 2, whereby the components of the parts washer 10 are readily accessible.

While certain of the embodiments of the present invention have been disclosed herein, other embodiments of the apparatus and methods of the present invention will suggest themselves to persons skilled in the art in view of this disclosure and the example below.

EXAMPLE: Ability of Invention to Clean Objects

Preliminary screening compared the washing ability of candidate cleaning fluids to mineral spirits. Two surfactant based cleaning fluids (also termed "fluids" or "solvents" herein) were preferred as a result. These two (Solvent #2 and #5 Table 1, were further tested for their ability to maintain viability of microorganisms suitable for biodegrading organic wastes in objects to be cleaned by the system, method and compositions of the present invention. Less preferred solvents were unable to clean substantially as well as mineral spirits. Tests were conducted using scrap parts obtained from auto repair shops (sites G, K, S, W, U in Table 1).

The cleaning (washing) effect of solvents alone was tested in 5 sites over several months wherein the solvents were used for washing parts in the routine course of business. Each solvent was tested over a period of several weeks to test efficacy of cleaning. Solvent #5 is Sea Wash 7. The build up of concentration of oil and grease was noted to rise steadily during the test period to the levels indicated. One liter samples of the fluid were removed at regular intervals and tested at an EPA certified testing laboratory to determine parts per million (ppm) of organic waste and particulate matter. Table 1a presents summary values (ppm) for two candidate solvents used in these tests, and the average ppm over the 5 sites.

Table 1a presents results of a compilation of data resulting from trials of the two cleaning fluids that gave the best results when tested prior to the introduction of microorganisms. Both solvents are water-based, non-toxic, surfactants.

Based on the tests comparing the solvents to the cleaning ability of mineral spirits and on the results in Table 1a, solvent #5 (Sea Wash 7) was selected to test with microorganisms. The same procedure used to generate Table 1a, was used, that is, solvent #5 and microorganisms were used to clean parts as a routine part of business at the same 5 sites. Approximately 7×10⁹ colony forming units were affoxed to a filter of dimensions of approximately 12×21 inches. Results in ppm of tests on one liter samples over time, show a dramatic effect of microorganisms on reducing the ppm.

Upon introducing microorganisms, the oil and grease concentrations dropped dramatically to the levels indicted in Table 1b. Laboratory tests indicated that it is possible to virtually eliminate oil and grease by continuing to circulate, aerate, and add microorganisms in fluid removed from use in parts washing. This suggested a compartment of the washing system that could be used to treat fluid and recirculate it to the compartment wherein objects are being washed.

Figure 5:
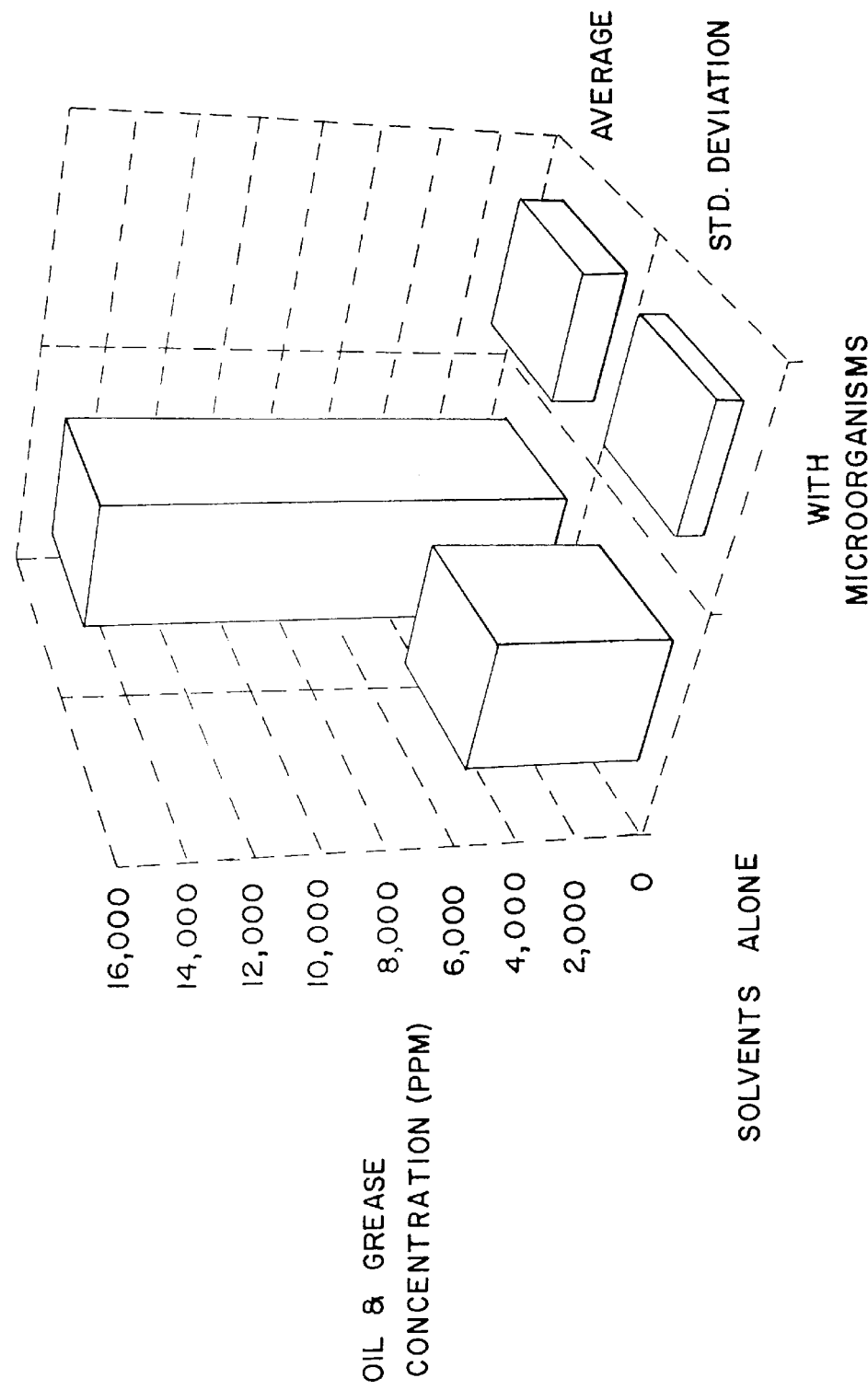
FIG. 5 illustrates the average ppm and standard deviation for oil and grease removed with and without microorganisms.
Figure 6:
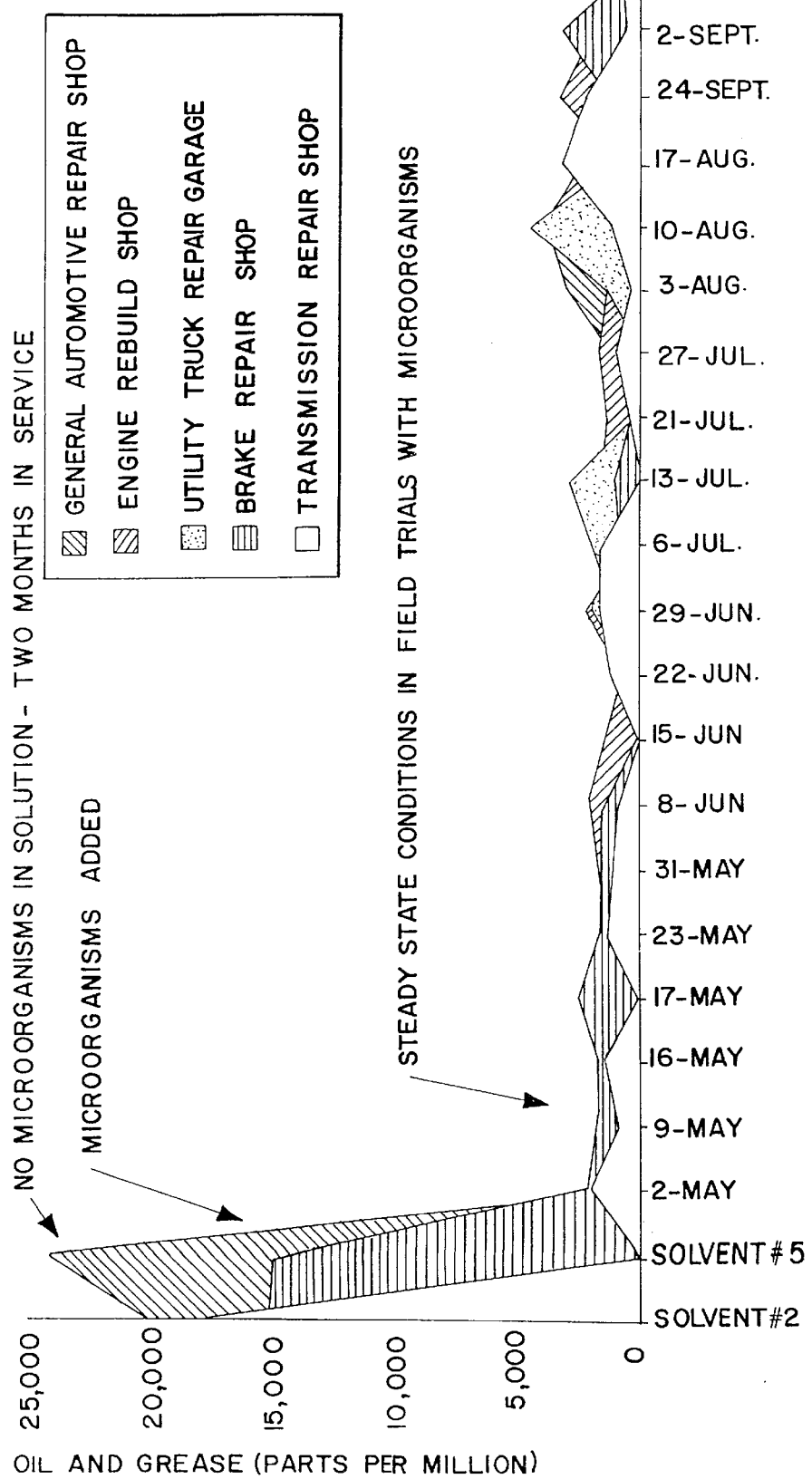
FIG. 6 illustrates the steady state in ppm over time during routine parts washing using solvent and microorganisms.

FIG. 5 shows a bar graph of the average ppm and standard deviation for solvent #5 alone compared to solvent #5 with microorganisms. FIG. 6 illustrates the steady state reached in a system of the present invention as determined by ppm of oil and grease detected by EPA criteria.

TABLE 1

OIL/GREASE STUDY-FIELD TEST SITES

Table 1a: DATA PRIOR TO INTRODUCTION Of MICROORGANISMS

| | OIL AND GREASE (ppm) | | | | | |
|---|---|---|---|---|---|---|
| | SITE G | SITE N | SITE S | SITE W | SITE U | Averages |
| Solvent #2 | 7,000 | 14,000 | 20,000 | 15,000 | 19,000 | 15,000 |
| Solvent #5 | 7,300 | 16,000 | 24,000 | 15,000 | | 15,575 |
| SITE AVE | 7,150 | 15,000 | 22,000 | 15,000 | 19,000 | 15,288 |

Table 1b: WITH MICROORGANISMS

| 1994 | OIL AND GREASE (ppm) | | | | | |
|---|---|---|---|---|---|---|
| MO DAY | SITE G | SITE N | SITE S | SITE W | SITE U | Averages |
| 5/2 | 1,000 | 2,500 | | 2,000 | 1,800 | 1,825 |
| 5/9 | 590 | | | 1,650 | 830 | 1,023 |
| 5/16 | 1,100 | 1,300 | | 1,600 | 1,300 | 1,325 |
| 5/17 | | | | 2,400 | | 2,400 |
| 5/23 | 720 | 670 | | 1,600 | 1,300 | 1,073 |
| 5/31 | 920 | 1,700 | | 1,500 | 1,000 | 1,280 |
| 6/8 | 1,300 | 2,000 | | 1,500 | 870 | 1,418 |
| 6/15 | 760 | 1,400 | | | | 1,080 |
| 6/22 | 410 | 610 | | 1,100 | 960 | 770 |
| 6/29 | 1,200 | 2,200 | 1,900 | 320 | 1,600 | 1,444 |
| 7/6 | 710 | | 1,900 | 730 | 1,500 | 1,210 |
| 7/13 | 1,800 | 1,200 | 2,800 | 970 | | 1,693 |
| 7/21 | 1,100 | 1,300 | | 310 | 400 | 778 |
| 7/27 | 1,100 | 1,600 | | 860 | 910 | 1,118 |
| 8/3 | 2,980 | 1,210 | 1,320 | 570 | 350 | 1,286 |
| 8/10 | 3,800 | 980 | 4,500 | 400 | 1,100 | 2,156 |
| 8/17 | 2,500 | 1,100 | 1,400 | 650 | 3,300 | 1,790 |
| 8/24 | 1,500 | 3,300 | 1,400 | 1,300 | 2,200 | 1,940 |
| 9/2 | 1,900 | 2,000 | 930 | 3,200 | 590 | 1,724 |
| 9/16 | 1,390 | 1,290 | 540 | | 730 | 988 |
| TOTAL ppm | 26,780 | 26,360 | 16,690 | 22,660 | 20,740 | |
| No of Tests | 19 | 18 | 10 | 19 | 18 | 84 |
| TOTAL ppm | 26,780 | 26,360 | 16,690 | 22,660 | 20,740 | 113,230 |
| AVERAGE | 1,409 | 1,464 | 1,669 | 1,193 | 1,152 | 1,348 |

KEY:
SITE G: General automotive repair shop
SITE N: Engine rebuilder
SITE S: Truck repair facility-utility compnany

TABLE 1-continued

OIL/GREASE STUDY-FIELD TEST SITES

SITE W: Brake repair shop
SITE U: Transmission repair facility

What is claimed is:

1. A closed system for cleaning automotive parts, equipment parts, and machinery parts with fouled organic matter, the system consisting essentially of
   (i) microorganisms that biodegrade organic matter in a surfactant fluid following activation, said microorganisms affixed prior to activation to
   (ii) a filter pack having a solid support and
   (iii) a surfactant fluid that cleans organic matter from the parts to produce
   (iv) a composition of surfactant fluid, microorganisms and organic matter, wherein said surfactant fluid activates and maintains the microorganisms from the filter pack that biodegrade the organic matter in
   (v) a receptacle, having a thermostatic heating element attached thereto to heat the cleaning fluid, said receptacle containing surfactant fluid, microorganisms and fouled organic matter, and
   (vi) adaptive fittings to create a recirculating biodegrading system to reform a surfactant fluid without fouled organic matter, and to nurture the biodegrading organisms, said surfactant fluid and said microorganisms being recycled to be available for cleaning of parts in separate locations.

2. The system of claim 1, wherein the parts are metal.

3. The system of claim 1, wherein the organic matter comprises oil, grease, ink, and grit.

4. The system of claim 1, wherein said microorganisms are capable of biodegrading hydrocarbons.

5. The system of claim 1, wherein said microorganisms are selected from the group consisting of the genus Bacillus, Micrococcus, Acinetobacter, Rhodococcus, Nocardia, Pseudomonas, Flavobacterium, Saccharomyces, Candida, and White Rot Fungus.

6. A conversion kit for parts washers that cleans fouled organic matter from metal and plastic parts, said kit consisting essentially of
   (a) a receptacle that contains a surfactant cleaning fluid which is suitable for cleaning said parts;
   (b) a filter pack comprised of a solid support, wherein microorganisms that biodegrade said organic matter are affixed to the support;
   (c) adaptive fittings to create a recirculating biodegrading system wherein the cleaning fluid cleans parts and, in a separate location, nurtures the biodegrading microorganisms, said fluid recirculating between said receptacle and a biodegrading location, wherein the biodegrading microorganisms are nurtured; and
   (d) a thermostatic heating element to heat the cleaning fluid to a temperature suitable for the microorganism.

* * * * *

UNITED STATES PATENT AND TRADEMARK OFFICE
CERTIFICATE OF CORRECTION

PATENT NO.    : 6,318,387 B1
DATED         : November 20, 2001
INVENTOR(S)   : James McClure et al.

It is certified that error appears in the above-identified patent and that said Letters Patent is hereby corrected as shown below:

<u>Title page,</u>
Item [73], The first assignee is incorrectly listed as "Advanced Bioremediation Systems." change the name of the Assignee to -- Zymo International, Inc. --

Signed and Sealed this

Fifth Day of November, 2002

*Attest:*

JAMES E. ROGAN
*Attesting Officer*   *Director of the United States Patent and Trademark Office*